United States Patent [19]
Keppel

[11] Patent Number: 5,159,928
[45] Date of Patent: Nov. 3, 1992

[54] METHOD AND APPARATUS FOR MEASURING AND CONTROLLING THE LEVEL OF HORMONES IN AN ANIMAL CIRCULATORY SYSTEM

[76] Inventor: William Keppel, 5027 Foothill Rd., Apt. E, Lake Oswego, Oreg. 97034

[21] Appl. No.: 440,977

[22] Filed: Nov. 22, 1989

[51] Int. Cl.$^5$ .............................................. A61B 5/00
[52] U.S. Cl. ................................... 128/630; 128/905
[58] Field of Search ...................... 128/630, 748, 905; 604/50, 52, 53; 424/9

[56] References Cited

U.S. PATENT DOCUMENTS

| | | | |
|---|---|---|---|
| 4,610,869 | 9/1986 | Bogden | 128/630 X |
| 4,823,808 | 4/1989 | Clegg et al. | 128/905 X |

FOREIGN PATENT DOCUMENTS

| | | | |
|---|---|---|---|
| 0935081 | 6/1982 | U.S.S.R. | 128/630 |
| 0957864 | 9/1982 | U.S.S.R. | 128/630 |
| 1442189 | 12/1988 | U.S.S.R. | 128/630 |

OTHER PUBLICATIONS

Harrison's *Textbook of Medicine* 10th Ed., McGraw-Hill N.Y. ©1983 pp. 776–777.
Spiegel, D. A. et al., "Effects of Psychosocial Treatment on Survival of Patients with Metastatic Breast Cancer", The Lancet Oct. 14, 1989 pp. 888–891.
Ward, M. et al. "Epinephrine and Norepinephrine Responses in Continuously Collected Human Plasma to a Series of Stresses", Psychosomatic *Medicine* vol. 45, No. 6, pp. 471–486 (Dec. 1983).
Hopkins, P. et al. "Identification & Rel. Wgt of CV Risk Factors" in *Cardiology Clinics* vol. 4, No. 1 Feb. 1986, pp. 3–31.
*Journal of Psychosomatic Research*, vol. 20, pp. 193–199 "Stressor Exposure and Immunological Response in Man: Interferon-Producing Capacity and Phagocytosis" Oct. 20, 1975.
Brain, Behavior, and Immunity, vol. 1, pp. 7–20 "Stress-Related Immune Suppression: Health Implications" 1987.
Journal Appl. Physiol., vol. 61(5), pp. 1869–1874 "Physiological Mechanisms Contributing to Increased Interleukin-1 Secretion" Jun. 9, 1986.
J. Appl. Physiol. vol. 61(5) pp. 1864–1868 "Metabolic Changes Following Eccentric Exercise in Trained and Untrained Men" Sep. 6, 1986.

*Primary Examiner*—Francis Jaworski
*Attorney, Agent, or Firm*—William A. Birdwell & Associates

[57] ABSTRACT

A method and apparatus for measuring and controlling the level of a selected hormone in the circulatory system of an animal. The relationship between the level of a hormone, such as the immune-regulating cylokine IL-1, in the blood stream of an animal and application of sensory stimuli to the animal is determined by periodically taking discrete samples of the animal's blood while the stimuli are applied, measuring the levels of the hormone in the discrete samples, and correlating these levels with the application of the stimuli. Thereafter, the level of the hormone is controlled by applying to the subject those stimuli have been found to produce a desired effect on the level of the hormone in the blood. Biofeedback training and relaxation techniques are used to increase the effectiveness of the method and apparatus.

25 Claims, 2 Drawing Sheets

METHOD AND APPARATUS FOR MEASURING AND CONTROLLING THE LEVEL OF HORMONES IN AN ANIMAL CIRCULATORY SYSTEM

BACKGROUND OF THE INVENTION

This invention relates to methods and systems for measuring and controlling the level of hormones in the circulatory system of an animal, particularly for controlling the level of immune-regulating cytokines such as IL-1, IL-2, and IL-6 ("IL" stands for interleukin) to reduce the likelihood of disease in human beings.

Certain substances in the blood stream of animals are known to have a powerful effect on the action of the immune system, and are involved in its modulation. These substances, which are hormones, include in the human being the immune-regulating cytokines IL-1, IL-2, and IL-6. Although these substances are measurable, their concentration per unit of blood volume is slight. Also, their concentration varies considerably over a relatively short period of time, in part because they have a relatively short half-life; that is, the time for the substance to reduce to one half its concentration is relatively short. Consequently, it has not previously been shown or believed that they vary in a reproducible way in accordance with external stimuli or behavioral action.

It would be desirable to be able to measure accurately the concentration of immune-regulating hormones in the blood stream and to determine how their concentration varies in relation to the application of external stimuli or behavioral action. This would enable the concentration of such hormones to be controlled so as to facilitate the body's ability to combat disease.

SUMMARY OF THE INVENTION

It has been discovered that the concentration of immune-regulating hormones, such as IL-1, in the blood stream over time can be measured accurately and does vary in accordance with behavioral action caused by external stimuli. This offers the possibility of influencing the immune function of an animal by the application of external stimuli. In particular, it offers the possibility of influencing the immune function of a human being through the use of guided imagery and suggestion in order to reduce the likelihood or effect of disease.

The present invention takes advantage of the aforementioned discovery by providing a method and system for accurately measuring the concentration of immune-regulating hormones in the blood stream over time in relation to the application of known sensory stimuli, and for controlling the concentration.

Samples of blood are taken from the subject periodically at known times. While the samples are being taken, one or more selected stimuli are supplied to the subject, also at known times. The concentration of a selected immune-regulating hormone in each sample is measured. The amount of the selected hormone in the samples is correlated with the time of occurrence of the selected stimuli supplied to the subject to identify the relationship between the stimuli and the level of the selected hormone.

Thereafter, to control the level of the selected immune-regulating hormone in the subject's body, the stimuli are applied in such a manner as to produce the desired effect on the concentration of immune-regulating hormone in the blood stream. Where the stimuli are guided imagery, the subject may be trained to form the influential images mentally, i.e., without external stimuli, and thereby control immune response so as to reduce the likelihood of disease.

During the measurement and control of the concentration of immune-regulating hormones, relaxation techniques are employed to increase the subject's concentration on the stimuli. This may be accomplished through biofeedback techniques, hypnosis, or other appropriate measures.

Therefore, it is a principal objective of the present invention to provide a novel and improved method and system for accurately measuring and controlling the level of immune-regulating hormones in the circulatory system of an animal subject.

It is another objective of the present invention to provide a method and system for accurately measuring the concentration of selected immune-regulating hormones in the blood stream of the subject over time, in response to known stimuli so as to determine the relationship therebetween.

It is a further objective of the present invention to provide a system for controlling the level of selected immune-regulating hormones in the blood stream of a subject through the use of imagined or real images presented to the subject in order to reduce the likelihood or effect of disease in the subject.

It is a principal feature of the present invention that it employs assays of blood samples taken periodically during the presentation of predetermined stimuli to a subject in order to determine the correlation between the presentation of the stimuli and the concentration of a selected immune-regulating hormone.

It is another principal feature of the present invention that it employs the selective presentation to a particular subject of images that have a known effect on the level of immune-regulating hormone in the particular subject in order to reduce the likelihood or effect of disease in the subject.

The foregoing and other objectives, features, and advantages of the invention will be more readily understood upon consideration of the following detailed description of the invention, taken in conjunction with the accompanying drawings.

DESCRIPTION OF THE PREFERRED EMBODIMENT

Figure 1:
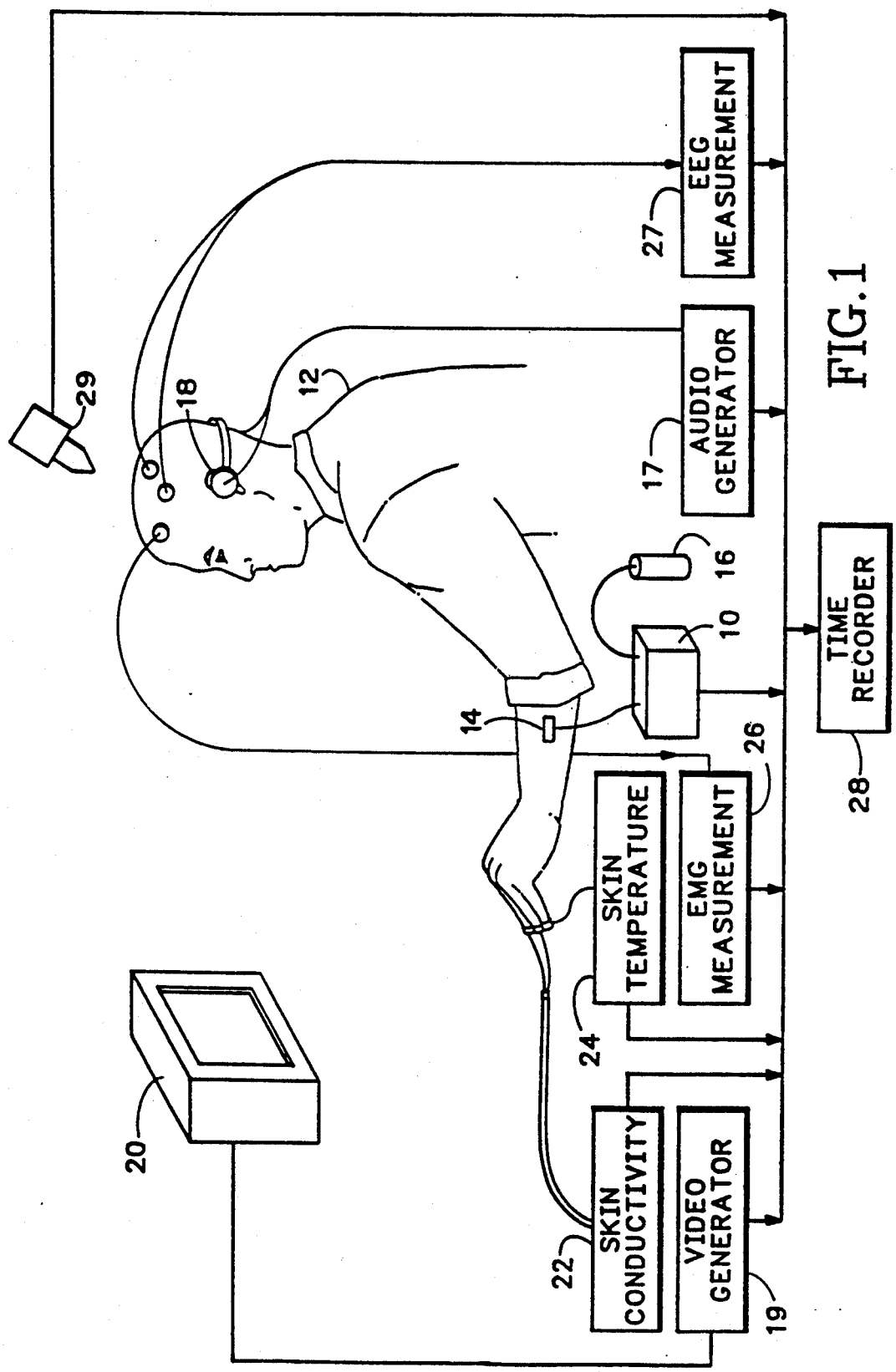
FIG. 1 shows a system for measuring and controlling the level of immune-regulating hormones in the blood stream of a human being in accordance with the present invention.

The existence and nature of a relationship between a stimulus and the level, or concentration, of an immune-regulating hormone in the blood stream of a human being can be found using a system of the type shown in FIG. 1.

In that system a continuous blood withdrawal apparatus 10 is connected to a human subject 12 by an intravenous catheter 14. This apparatus is used to take periodic samples of the blood for measurement of the concentration of a selected immune-regulating hormone therein. The continuous blood withdrawal apparatus may be any of a variety of commercial products commonly known to health practitioners. For example, it may be a Model ML-6-5L Constant Blood Withdrawal Pump marketed by Cormed, Inc., 591 Maher Street, Medina, N.Y. 14103. The catheter 14 is preferably a 25 ga catheter, and would ordinarily be placed in a large forearm vein. A thrombo resistant coating of the catheter is used to prevent blood clotting during removal, as is commonly understood by practitioners. Such a non-thrombogenic catheter is also available from Cormed, Inc. The apparatus 10 is used to remove blood from the blood stream for sampling at predetermined intervals, while running at a "keep open" rate when active sampling is not in process. That is, for example, samples of about 3 ml may be taken every 6 minutes, and when samples are not being taken blood is withdrawn at a rate of about 2 ml per hour. Samples 16 are collected for assay of the blood.

In addition to the continuous blood withdrawal apparatus 10, the system of FIG. 1 includes one or more sources of stimulus and, preferably, electrophysiologic monitoring equipment. The sources of stimulus may be, for example, an audio generator 17, e.g., an audio tape player, connected to earphones 18 worn by the subject, or a video generator 19, e.g., a video cassette recorder ("VCR"), connected to a video monitor 20. The electrophysiologic monitoring equipment may be, for example, a device 22 connected to the subject's fingers in a standard way for measuring skin conductivity, a device 24 also connected to the subject's finger in a standard way for measuring skin temperature, an electromyogram ("EMG") measurement device 26 for measuring muscle tension, an electroencephalogram ("EEG") device 27 for measuring brainwave frequency characteristics or electric evoked potentials, or a magnetoencephalogram ("MEG") apparatus 29 for measuring magnetic evoked potentials and localized electrical activity of the brain. Preferably, each of the electrophysiologic measurement devices is also connected to a time recorder 28 to record the time when physiologic events occur, when samples are taken, and when selected stimuli are presented. The electrophysiologic monitoring equipment may be used to provide biofeedback to the sources of stimulus to induce relaxation of the subject, or to provide additional correlatives with the level of immune-regulating hormone in the blood stream.

In a preferred implementation of the diagnostic procedure of the present invention the continuous blood withdrawal apparatus 10 is attached to subject 12 by the intravenous catheter, and blood samples 16 are taken every 6 minutes. The subject is provided with earphones 18 connected to a source of a prerecorded audio message, i.e., audio generator 17. Typically a tape player would be used. Skin conductivity, skin temperature, EMG, and electrical or magnetic evoked potentials may, but need not necessarily, be monitored. A series of predetermined audio messages is begun with the blood sampling, and the time is monitored. The messages are selected from among messages believed to be effective in producing desired changes in the level of IL-1. The samples are correlated with the time. For each sample, the serum is separated from the whole blood and analyzed for IL-1.

Blood samples are collected, e.g., in a polyetheylene apparatus, according to a sterile technique and refrigerated immediately, typically at about 35°-60° F. until it is needed for further processing. Serum is separated from whole blood under a sterile range hood according to a sterile technique after being centrifuged at 3500 RPM for 15 minutes. Preferably, the serum is then ultra centrifuged in polyethylene cryogenic vials at 8000 RPM for 20 minutes. Where processing is interrupted, the serum should be frozen at −80° C. until processing resumes. At a convenient time, the serum is thawed and tested for the IL-1 level by incubation with a D-10 IL-1 dependent indicator cell assay system of a type commonly known to laboratory immunologists. The IL-1 present is proportional to the number of radioactive counts per minute of a radioactive tracer detected from the indicator cells at the completion of the test. This test preferably should be accurate for levels of IL-1 approximately as low as 1-5 picograms per cc.

Ordinarily, two conditions must be met for the method described hereafter to work. First, the subject must be capable of relaxation as measured by skin conductivity, skin temperature, EMG, brainwave frequency control, or other useful means, such that attention to behavioral intervention, such as a set of guided imagery, is possible. Second, there must exist guided images to which the subject will be responsive—as revealed by blood testing. The universe of guided images to which a person might respond is best selected by the person him or herself. Some persons respond positively to certain images and negatively to others, depending on their history. The blood testing together with trials of old and new images allows the most effective images to be identified. The results are plotted and compared to the stimuli administered over the same time period to identify the most effective images.

Figure 2:
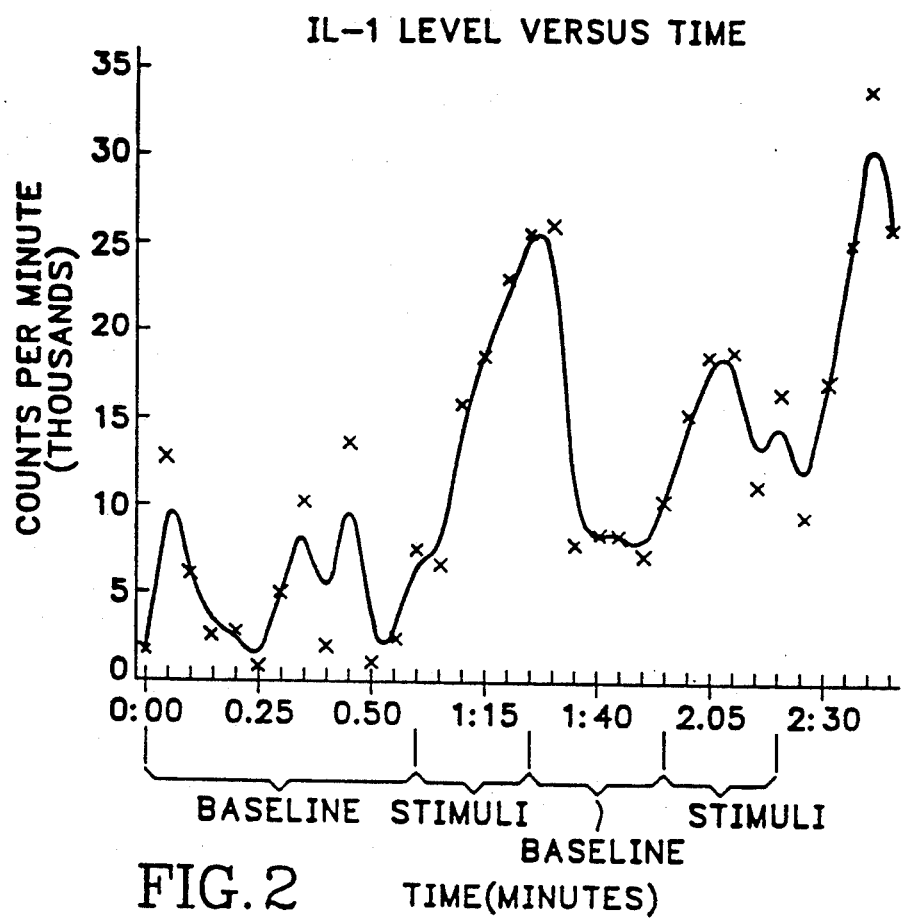
FIG. 2 shows an exemplary graph of the relationship between the presentation of a first set of selected stimuli and the level of the immune-regulating hormone IL-1 in the blood stream of one particular human being.

In the exemplary implementation represented by FIG. 2, the procedure lasts about two and one-half hours. During the first hour, measurements are taken to establish a baseline. The subject is given a neutral suggestion regarding the use of this time, like: "Use this time in any quiet activity you wish. Reading, watching television, organizing files, paying bills, making routine phone calls are all acceptable."

For the next twenty-five minutes, the subject is given the suggestions described in Chart 1.

| Chart 1 | |
|---|---|
| Time (in minutes) following initial baseline | Stimulus |
| 0-11 | Images of heaviness, warmth and relaxation progressively throughout the body, from toes to head |
| 11-12 | Focusing on the darkness at the back of the eyelids and centering one's self in the head |
| 12-16 | Continuation of whole body relaxation, warmth and heaviness |
| 16-17 | Re-living a happy moment from the past and feeling confident and strong |
| 17-19 | Remembering getting well after an illness, feeling vigorous |
| 19-20 | Mentioning having a favorite |

Chart 1

| Time (in minutes) following initial baseline | Stimulus |
| --- | --- |
| 20-25 | dream come true five years in the future Feeling quiet, relaxed, comfortable, warm and heavy |

The text of the narrative for the suggestions in Chart 1 reads as follows:

0-11 Minutes

General relaxation breathing suggestion

"Find a comfortable position in which your body feels at ease. Begin by taking several deep breaths in the following way. Breathe into your stomach, letting it rise like a balloon. Inhale into the stomach, and then into your chest. Exhale from the chest. Then deflate the stomach. Practice this several times at your own pace."

Pause

Progressive relaxation exercise with which the subject has had prior experience

"You may now focus your attention on your body, and repeat the following phrases to yourself silently.

'I feel quite quiet. I am beginning to feel quite relaxed. My feet feel heavy and relaxed. My ankles, knees, and hips feel heavy, relaxed, and comfortable. The central portion of my body feels relaxed and quiet. My shoulders, arms, and hands feel heavy, relaxed, and comfortable. My neck, my jaws, and my forehead, feel relaxed, comfortable, and smooth. My whole body feels quiet, heavy, comfortable, and relaxed.'"

Pause

Continuing progressive relaxation

'I feel quite quiet. I am feeling quite relaxed. My feet feel heavy and relaxed. My ankles, knees, and hips, feel heavy, relaxed, and comfortable. The central portion of my body feels heavy, relaxed, and comfortable. My shoulders, arms, and hands, feel heavy, relaxed, and comfortable. My neck, my jaws, and my forehead, feel relaxed. They feel comfortable and smooth. My whole body feels quiet, heavy, comfortable, and relaxed. I am quite relaxed. My arms and hands are heavy and warm. I feel quite quiet. My whole body is relaxed. Warmth is flowing into my hands. I can feel the warmth flowing down into my arms and into my hands. I can feel the warmth flowing down into my legs and into my feet. My hands are warm, relaxed, and warm. My feet are warm. My whole body feels quiet, comfortable, and relaxed. My mind is quiet. I withdraw my thoughts from the surroundings and I feel serene and quiet. My thoughts are turned inward and I am at ease. Deep within my mind I can visualize and experience myself as relaxed, comfortable, and still.'

11-12 Minutes

Image of darkness behind eyelids

'I notice the darkness on the back of my eyelids. From this vantage point I can go inside, behind the back of my eyelids, back to the center of my head. A warm, dark, secure, quiet, vantage point. With each breath, the darkness gets deeper. My body feels quite relaxed. I feel quite quiet, relaxed.'

12-16 Minutes

Continuing relaxation

'My whole body is relaxed. My hands and feet are relaxed and warm. My whole body feels quiet, comfortable, and relaxed. My mind is quiet, my thoughts are turned inward and I am at ease. Deep within my mind I can visualize and experience myself as relaxed, comfortable, and still. I am alert but in an easy, quiet, inward-turned way. I feel life and energy flowing through my legs, hips, central portion of my body, chest, arms, hands, neck, and head. The energy makes me feel light and alive.

'My body feels quite relaxed. I feel quite quiet, quite relaxed. My whole body is relaxed. My hands and feet are relaxed and warm. My whole body feels quiet, comfortable, and relaxed. My mind is quiet. My thoughts are turned inward and I am at ease. Deep within my mind I can visualize and experience myself as relaxed, comfortable, and still. I am alert but in an easy, quiet, inward-turned way. My mind is calm and quiet. I feel an inward quietness.'

16-17 Minutes

Specific happy memory

'I am remembering now a happy moment in my life. The happiest one that I can think of, allowing myself to relive it with as much detail as I can. I can see and feel how old I am, the surroundings, who is with me, and all the thoughts and feelings of the moment. I feel confident and strong, happy and alert, light and alive.'

17-19 Minutes

Suggestion of remembering a specific time where subject's immune function would have to have been at a relative peak, i.e., an immune image 'I am now beginning to remember a time when I was getting well after an illness. I am picturing to myself the details that come to mind. I can see how old I am, where I am, what the room looks like, who I am with, and what a relief it is to be well again. How good it feels to be well. To feel vigorous again, to breathe easily and effortlessly, to feel strong, to think clearly, to taste and smell again. The illness has been just a speck of dust, easily wiped away by my immune system, my powerful collection of immune cells. It feels so good to be healthy now. Quietly relaxed, energetic, having powerfully rid myself of this problem, a tiny problem so small compared to the power of my million immune cells, that vast intelligent force. My body is wise and powerful in fighting disease. I can feel the vitality, the strength, the confidence to go on with life as usual. It feels so wonderful to be well again. I feel confident and strong, happy and alert, ready to meet new challenges, light and alive.'

19-20 Minutes

Suggestion of hopeful image specific to the subject

'I'm now imagining being 5 years into the future. My favorite dream has come true. How good that feels. I look back to today's date and marvel, how things that once seemed impossible or nearly impossible actually have materialized and are now a matter of everyday life. It feels wonderful to have achieved my goal.'

20–25 Minutes

End of relaxation imagery and suggestion to maintain the relaxed state

'My whole body feels quiet, comfortable, and relaxed. Deep within my mind I can visualize and experience myself as relaxed, comfortable, and still. I am alert but in an easy quiet, inward-turned way. My mind is calm and quiet. I feel an inward quietness. I feel life and energy flowing through my legs, hips, central portion of my body, chest, arms, hands, neck, and head. The energy makes me feel light and alive.'"

At one hour and twenty-five minutes into the tape, the baseline instructions are repeated, that is: "Use this time in any quiet activity you wish. Reading, watching television, organizing files, paying bills, making routine phone calls are all acceptable." Thirty minutes later, the imagery of Chart 1 is also repeated for twenty five minutes. The subject is given no further suggestions and the procedure is terminated after about two and one-half hours.

It can be seen from FIG. 2 that the level of IL-1 varies with the application of different stimuli. When normal quiet activity is suggested, the level of IL-1 remains or becomes relatively low, while suggestions chosen to stimulate IL-1 production cause the level of IL-1 to go up. That is, during the first hour, the IL-1 level fluctuates up and down in a statistically insignificant amount. During the following twenty five minutes of imagery, the level of IL-1 rises continuously. Then, when normal activity is again suggested for thirty minutes, it falls down. Thereafter, with the re-application of positive stimuli, the level of IL-1 again rises. A particular benefit is that there may be, as in this case, a residual effect whereby the level of IL-1 rises or remains high even after the procedure has been completed, as shown by the last twenty-five minutes of the graph in FIG. 2. This effect may be produced by ending the audio stimuli and procedural session with positive suggestions.

Figure 3:
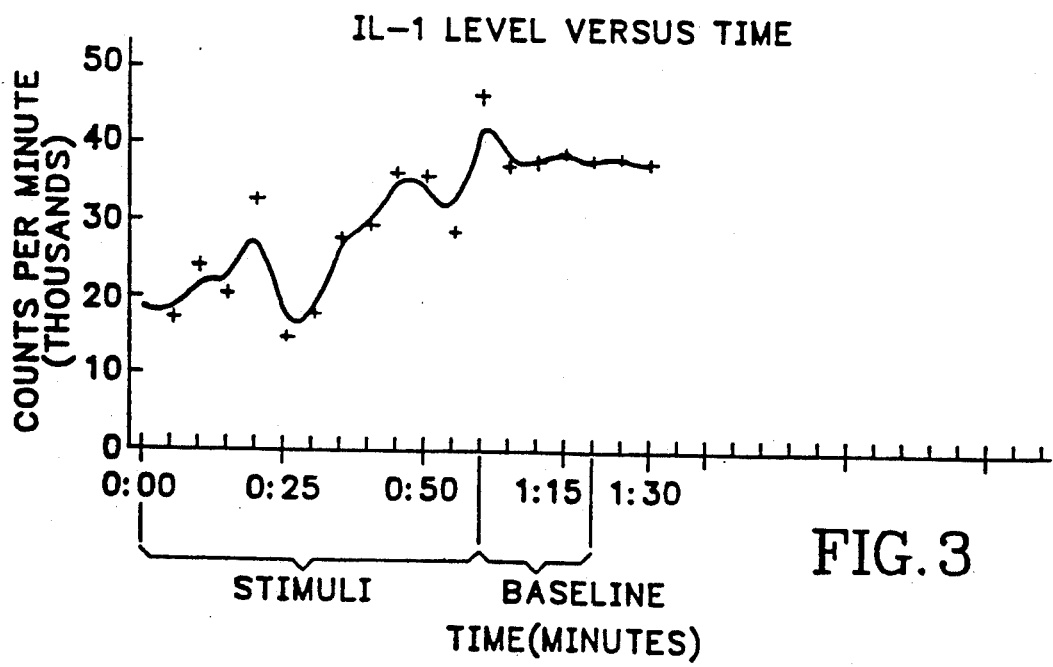
FIG. 3 shows an exemplary graph of the relationship between the presentation of a second set of selected stimuli and the level of the immune-regulating hormone IL-1 in the blood stream of another particular human being.

In the exemplary implementation represented by FIG. 3, the procedure lasts about one and one-half hours. In this case, a baseline is not found initially. During the first fifty-eight minutes audio stimuli are provided. Then, a baseline is measured for thirty minutes. This graph represents the results based on the audio stimuli described in Chart 2.

Chart 2

| Time (in minutes) following initial baseline | Stimulus |
| --- | --- |
| 0–12 | Relaxation images |
| 12–15 | Immune images |
| 15–16 | Happy moments images |
| 16–28 | Relaxation images and end of relaxation reverie |
| 28–33 | White light images |
| 33–35 | Darkness images and deep security images |
| 35–37 | Immune images |
| 37–39 | Darkness images with wisdom images and recovery memories |
| 39–41 | Happy moment memories and darkness images |
| 41–47 | Pleasant hypnotic images |
| 47–50 | Hypnotic images with picturing being able to solve difficult problems |
| 50–53 | Immune images plus images of vitality |
| 53–55 | Immune images |
| 55–56 | Imaging confidence regarding getting over disease |
| 56–58 | End of hypnotic imagery |

The text of the narrative for the suggestions in Chart 2 reads as follows:

0–12 Minutes

Relaxation images

"Find a comfortable position in which your body feels at ease. Begin by taking several deep breaths in the following way. First, breathe into your stomach, letting it rise like a balloon as you inhale, gently allowing your chest to expand after your stomach does. First fill the stomach balloon, then the chest balloon, then gradually as you exhale allow the chest balloon to deflate first, followed by the stomach balloon. Inhale into the stomach and then the chest. Exhale from the chest, then deflating the stomach. Allow yourself to practice this several times at your own pace."

"Now, if you wish, you may focus your attention on your body and repeat the following phrases to yourself, silently, 'I feel quite quiet, I am beginning to feel quite relaxed. My feet feel heavy and relaxed. My ankles, my knees, and my hips, feel heavy, relaxed, and comfortable. My solar plexus and the whole central portion of my body feel relaxed and quiet. My hands, my arms, and my shoulders feel heavy, relaxed and comfortable. My neck, my jaws, and my forehead, feel relaxed. They feel comfortable and smooth. My whole body feels quiet, heavy, comfortable, and relaxed.'

"Continue alone for a moment."

'I am quite relaxed. My arms and hands are heavy and warm. I feel quite quiet. My whole body is relaxed and my hands are warm, relaxed and warm. My hands are warm. Warmth is flowing into my hands; they are warm—warm. I can feel the warmth flowing down my arms into my hands. My hands are warm, relaxed and warm.'

"Continue alone for a minute."

'My whole body feels quiet, comfortable, and relaxed. My mind is quiet. I withdraw my thoughts from the surroundings and I feel serene and quiet. My thoughts are turned inward and I am at ease.'

'Deep within my mind, I can visualize and experience myself as relaxed, comfortable, and still. I am alert but in an easy, quiet, inward-turned way. My mind is calm and quiet. I feel an inward quietness.'

"Continue alone for a minute."

'My mind is calm and quiet. My feet feel heavy and relaxed. My ankles, my knees, and my hips, feel heavy, relaxed, and comfortable. My solar plexus and the whole central portion of my body feel relaxed and quiet. My hands, my arms, and my shoulders, feel heavy, relaxed, and comfortable. My neck, my jaws, and my forehead, feel relaxed. They feel comfortable, and smooth. My whole body feels quiet, heavy, comfortable, and relaxed.'

"Continue alone for a minute."

'I am quite relaxed. My arms and hands are heavy and warm. I feel quite quiet. My whole body is relaxed and my hands are warm, relaxed and warm. My hands are warm. Warmth is flowing into my hands. They are warm. Warm.'

'I can feel warmth flowing down into my arms and into my hands. My hands are warm, relaxed, and warm.'

"Continue alone for a minute."

'My whole body feels quiet, comfortable, and relaxed. My mind is quiet. I withdraw my thoughts from the surroundings and I feel serene and quiet. I am alert but in an easy, quiet, inward-turned way. My mind is calm and quiet. I feel an inward quietness.'

12-15 Minutes

Immune images

'Now, from this vantage point, I am beginning to remember a time when I was getting well after an illness I am picturing to myself the details that come to mind. I can see how old I was, where I was, what the room looked like, who I was with. What a relief it is to be well again. How good it feels to be well. To feel vigorous again. To breathe easily and effortlessly. To feel strong, to think clearly, to taste and smell again. The illness was just a speck of dust, easily wiped away by my immune system—my powerful collection of immune cells. It feels so good to be healthy now—quietly relaxed, energetic, having powerfully rid myself of this problem, a tiny problem, so small in the face of the power of my million immune cells—the vast intelligent force. My body is wise and powerful in fighting disease.'

"Continue picturing this time of getting well."

15-16 Minutes

Happy moment image

'My attention now shifts to another happy moment of my life—the happiest time that comes to my mind. I may relive it as fully and with as much detail as comes to mind and enjoy it for another few minutes.'

16-28 Minutes

Relaxation image and end of reverie

'My mind is calm and quiet. I feel an inward quietness. Deep within my mind I can visualize and experience myself as relaxed, comfortable, and still. I am alert but in an easy, quiet, inward-turned way. My mind is calm and quiet. I feel an inward quietness. My hands are warm, relaxed, and warm. My whole body feels quiet, comfortable, and relaxed. My thoughts are turned inward and I am at ease.'

"Continue alone for a minute."

'I feel life and energy flowing through my legs, hips, solar plexus, chest, arms, hands, neck and head. The energy makes me feel light and alive. I feel quite quiet. I am beginning to feel quite relaxed.'

'My feet feel heavy and relaxed. My ankles, my knees, and my hips, feel heavy, relaxed, and comfortable. My solar plexus and the whole central portion of my body feel heavy, relaxed, and quiet. My hands, my arms, and my shoulders, feel heavy, relaxed, and comfortable. My neck, my jaws, and my forehead, feel relaxed. They feel comfortable and smooth. My whole body feels quiet, heavy, comfortable, and relaxed.'

"Continue alone for a minute."

'I am quite relaxed. My arms and hands are heavy and warm. I feel quite quiet. My whole body is relaxed and my hands are warm. Warmth is flowing into my hands. They are warm, warm. I can feel the warmth flowing down my arms into my hands. I can feel the warmth flowing down my legs into my feet. My hands are warm, relaxed and warm. My feet are warm.'

"Continue alone for a minute."

'My whole body feels quiet, comfortable, and relaxed. My mind is quiet. I withdraw—my thoughts are turned inward—and I am at ease. Deep within my mind, I can visualize and experience myself as relaxed, comfortable, and still. I am alert but in an easy, quiet, inward-turned way. My mind is calm and quiet. I feel an inward quietness.'

"Continue alone for a minute.

"The relaxation and reverie is now concluded and the whole body is reactivated with a deep breath and the following phrases: 'I feel life and energy flowing through my legs, hips, solar plexus, chest, arms and hands, neck and head. The energy makes me feel light and alive.'"

17 Minutes

Discontinuity

Pause

"Allow yourself to find a comfortable position in which your body feels at ease. Allow yourself to sink into the surface where you rest. Begin by taking several deep breaths in the following way. First, breathe into your stomach, letting it rise like a balloon as you inhale; gently allow your chest to expand after your stomach does. First fill the stomach balloon, then the chest balloon, then gradually as you exhale allow the chest balloon to deflate first followed by the stomach balloon. Inhale into the stomach and then the chest. Exhale from the chest and then the stomach. Practice this several times at your own speed.

"You may be noticing other distractions; simply let them pass by and maintain the awareness of your breathing. You may notice yourself beginning to relax."

28-33 Minutes

White light images

"Now, beginning with your toes, imagine that you are gently relaxing each bone in your body. Beginning with the toes, gently separate each bone from the next. As you do so, imagine that your bones are as light as those of a sparrow, and imagine at each joint clear white light emanating from the space between the bones as if you are filled with white light. Proceed from your toes to your arches and your heels to your ankle bones, your knees; gradually rising through your body. Imagine each bone as light as air. Imagine a clear shaft of light rising through your body, evidenced at each joint where it escapes. Proceed now to your hips and spine. At the lower end of your spine, gently separate each vertebra. Allow the column of light and relaxation to rise up your spine, gently relaxing and separating each vertebra. As you come to your ribs, imagine the light filling each one, emanating from your chest where the ribs meet. Continue with the awareness of your body and each bone as gently being separated from the next. Continue to your shoulder blades, your elbows, wrists, hands, fingers. Proceed through your neck. Visualize the light shining forth from each of the joints in you body. Continue to your head. Imagine the light coming out of the top of your head. Gently separate the parts of your head from one another; your ears, nose, eyes, mouth, are gently detached. Your skin feels warm and waxy. Feel the warm, waxy, sensation flowing gently over your face, over your body—flowing down—warm—warm—to your toes, to your hands."

33-35 Minutes

Darkness and security images

"Now, if you wish, you may focus your awareness on the darkness on the back of your eyelids. If the darkness varies, that's all right. Notice how it tends to get lighter and darker again. From this vantage point, allow yourself to go inside, behind the back of your eyelids—back—back to the center of your head. Perhaps this will seem a warm, dark, secure, quiet, vantage point. Your body may be feeling quite light and relaxed at this time.

"With each breath, you may notice the darkness getting deeper It may begin to seem as if it is nightime—a time of becoming more deeply relaxed and secure. Waves of darkness and security and warmth or other sensations may occur. You can simply watch them all from this safe, secure vantage point. You are safe here from all of your problems; all are far, far away. This is a clear, collected spot from which to observe. Allow yourself, if you wish, to enjoy this experience for a few minutes, remembering you can return here whenever you wish, be it for a moment between breaths or for an hour."

35-37 Minutes

Immune images

"Now, from this vantage point, if you wish, you may recall a specific memory related to your health. Perhaps there was a time when you were getting well after an illness. It may have been a minor illness, such as a cold sore or influenza, or a more serious illness—any such illness that easily comes to mind. You may picture how old you were, where you were, what the room looked like, or who was with you. You may picture it as clearly to yourself with whatever details come to mind and notice particularly what a relief it was to be well again after that illness. How good it feels now, as you picture the time of getting well, to feel vigorous again, to breathe easily and effortlessly, to feel strong, to think clearly, to taste and smell again. This illness was simply a speck of dust easily brushed away by your powerful immune system—the powerful army of immune cells. It feels so good to be healthy now, quietly relaxed, energetic—enjoy this feeling. Life may throw you other kinds of problems, too, now or in the future, but be secure in this knowledge that you are powerful and handle difficulties well as you did in recovering from this puny illness, now past, now long past."

37-39 Minutes

Darkness image with wisdom images and recovery memories

"Remember this calm, quiet place, deep behind your eyes, dark and warm. You can return here whenever you wish. You may let it sustain you as time goes by. You may use it to help with current problems of any kind. Come here between breaths during the day or even when you sleep at night. It is your power that produces this feeling of calm, collected, wisdom and you can use it in any way you wish. You have, in fact, used this vantage point all of your life already, perhaps without even knowing it.

"Very briefly, again, picture the illness you thought of earlier and quickly review the experience of being well, having powerfully rid yourself of the problem—a tiny problem, so small in the face of the power of your million immune cells, the vast intelligent immune force. Your body is wise and powerful in fighting disease. It has done so many, many times."

39-41 Minutes

Happy moment memories darkness images

"Remember, now, if you wish, a happy moment in your life—the happiest moment that comes to mind. Allow yourself to relive it as fully and with as much detail as comes to mind. Take a few moments to do so.

"This vantage point deep behind your eyes may allow greater clarity of memory. Simply allow yourself to reexperience this happy time in your past. Enjoy it for another few moments."

41 Minutes

Discontinuity

41-47 Minutes

Pleasant hypnotic images

"Now, if you wish, you may listen to the sound of my voice. Simply let it guide you, let it anchor you to the ground. Now, if you wish, imagine that you are floating in the sky. It is springtime. The warm air carries you aloft, like a kite. Simply let my voice anchor you firmly to the ground.

"The earth is far below. You can hear the sounds of children playing and feel warm and contented, away from all of life's problems. Simply floating pleasantly in the air. Letting my voice be the anchor.

"Now, if you wish, imagine an old oak staircase in a large old house. There are 20 steps to this staircase and there is a rich purple carpet covering the stairs. With each step you take, you will become a bit more deeply relaxed. Simply listen to the sound of my voice. The old oak bannister has been traveled down by many, many people in the past who have used it to get more and more relaxed. As I count to 20, you can take yourself down the staircase if you wish—simply letting my voice anchor you. 1 ... 2 ... 3 ... deeper and deeper relaxed ... 4 ... 5 ... 6 ... deeper and deeper relaxed ... 7 . .. 8 ... 9 ... 10 ... halfway to the bottom of the staircase ... more and more deeply relaxed ... 11 ... 12 . .. 13 ... 14 ... deeper and deeper relaxed. If you feel any muscle tension or hear sounds that are distractions, simply let them pass through ... 15 ... 16 ... 17 ... deeper and deeper relaxed ... 18 ... 19 ... 20. Imagine that you are standing in a beautiful room. There are several doorways across the way. Allow yourself, if you wish, to walk across the room and open one of the doors. As you enter the next room, you will see a window that opens on a meadow. Allow yourself to walk across the room, open the door and go outside, if you wish. It's a nice spring day, the temperature is perfectly warm. There is an old oak tree about a hundred feet away. Allow yourself, if you wish, to go over and sit down next to the old oak tree. The old oak tree has been there for many years and is very wise. Its roots go deeply into the earth. It has seen many people and situations come and go, and, as you lean against it, allow yourself, if you wish, to draw from its strength and wisdom, having been there for so long. You may find that simply sitting next to this oak tree, you feel stronger and it helps you get in touch with the wise part of yourself. The old oak tree is very wise and can help solve problems. If not now, perhaps in the days to come, solutions to problems you have been working on may come to your mind as a result of sitting here next to the old oak tree. You may in the future, if you wish, return to this old oak tree in your imagination and use it for strength and wisdom. Simply allow yourself to sit there, leaning on the old oak tree, gathering its wisdom and security.

"Now, in a moment, if you wish, it may seem as if a great deal of time has passed and you have become refreshed and more secure than you felt in the past simply by sitting next to the old oak tree and as you get up to walk back to the house, notice what a good feeling this has been and that you can take some of it with you, as much as you wish."

47-50 Minutes

Hypnotic images with picturing being able to solve difficult problems

"Now, return to the house. Open the door. Notice that there is a picture on the wall in the room that you entered. It is a picture relating to yourself and your current situation and it has some sort of a solution to your problems in it. It may be of symbolic nature. Allow yourself to walk over and look at this picture. In the days ahead, you may be able to use this picture and any symbolism in it to help you solve the problems facing you at the moment.

"Now, allow yourself to go through the doorway, back to the entry hall at the bottom of the stairway, to the large room at the bottom of the stairs. You may notice another doorway to another room. Allow yourself to pass over to the doorway, if you wish, and step inside. Picture, if you wish, a continuation of the thick, beautiful, purple carpet and the richly paneled walls. There are several easy chairs in this room and, if you wish, you may allow yourself to sit in one of them."

50-53 Minutes

Immune images plus images of vitality

"You may find yourself, if you wish, musing on a memory from the past related to an illness from which you fully recovered. Allow yourself, if you wish, to remember as fully as possible the details of your recovering from this illness, now long past. Although you had been ill, notice how good it feels now remembering the days surrounding your recovery, how good it feels to be able to smell and breathe freely again, to feel strong and confident. Your powerful immune system brushed away this illness as if it were a speck of dust, no match at all for your powerful army of immune cells.

"Allow yourself to simply remember the good feeling of being recovered from an illness. No matter how uncomfortable you had been feeling during the illness, at this point of recovery it feels wonderful to be well again.

"Allow yourself to fully appreciate how good it feels to be perfectly well again.

"Feel the vitality, the strength, the confidence to go on with your life as usual."

53-55 Minutes

Immune images

"Allow yourself now, if you wish, to remember yet another illness that you fully recovered from.

"Allow yourself, if you wish, to remember the people surrounding you in the days of recovery. Perhaps you can recall what the room looked like, what you were thinking about, perhaps what you had for breakfast. You may recall any other details that come to mind if you wish."

55-56 Minutes

Image of confidence regarding getting over disease

"Again, notice how good it feels to be fully well again. To smell and breathe freely; to feel confident and strong. To feel happy and alert. Ready to meet new challenges. Your powerful immune system, millions of cells, easily wiped away the illness as if it were a speck of dust—no match for your body. Allow yourself to delight in how powerful the process was in taking care of you. Feel how good it is. Enjoy the sense of confidence that your immune system protects you and how strong and confident you can feel. Simply lean back and enjoy the feeling of calm confidence. Your body has protected you, defended you, taker care of you many, many times in the past.

"Simply allow yourself to breathe freely—inhale relaxation—exhale tension with each breath." 56-58 Minutes

End of hypnotic imagery

"You may begin to think about getting up from the easy chair in the room with the purple carpet and the wood paneling where you sit. In a moment, you may do so and return to the doorway, passing through back toward the staircase. Allow yourself to walk over to the bottom of the staircase, grasping the old oak handrail, and as you begin to climb back up the stairway, you will be going toward your usual state of awareness.

"As I count backward from 20, you will begin ascending the staircase if your wish. 20 . . . 19 . . . 18 . . . 17 . . . 16 . . . 15 . . . 14 . . . 13 . . . 12 . . . 11 . . . 10 . . . halfway to your usual state of awareness if you wish to return there . . . 9 . . . 8 . . . 7 . . . 6 . . . 5 . . . 4 . . . when we reach one, you may begin opening your eyes and returning to your usual state of awareness . . . 3 . . . 2 . . . 1. You can open your eyes now if you wish."

It can be seen from the graph of FIG. 3 that the level of IL-1 varies depending on the particular stimulus applied, and it can thereby be determined for the subject which of the various stimuli are most likely to increase the level of IL-1. For example, from about the twenty fifth minute to about the forty fifth minute, the level of IL-1 increases. Since IL-1 has a half life of only about 3 minutes, it can be concluded that some stimuli applied during the period 20 minutes to 40 minutes tend to cause the subject to produce more IL-1. On the other hand, from about 45 to 50 minutes, IL-1 decreases. It can therefore be concluded that some stimuli applied during the period forty to fifty minutes do not tend to cause an increase of IL-1 in the subject, and may even reduce the level of that hormone. (While the tape used to produce the results shown in FIG. 3 contained no statements designed to suggest aversive images, it did contain discontinuities—places where the topic shifts dramatically or where a loud noise occurs—which simulate the effect of an aversive suggestion. These occur at 17 minutes and 41 minutes, which correlate with decline in the IL-1 level.) In this way, stimuli that cause the IL-1 level to increase in the particular patient can be identified and later used on a selective basis to help the subject combat illness.

In some cases a single exposure to stimuli, e.g., a single playing of the tape, results in a physiological change in IL-1 level. In other cases preliminary training is needed. Generally, it has been found that some combination of the following training procedures is ordinarily needed for effective use of the procedures of this invention:

1. more than one exposure to the stimuli;
2. one or more hypnotic induction sessions, as described below;
3. preliminary training in skin temperature biofeedback training such that the subject's skin temperature can be brought to above 94° Farenheit measured by a common electronic thermometer;
4. preliminary training in frontalis EMG relaxation biofeedback such that resting muscle activity is reduced below 1.0 microvolt RMS, or a similar muscle group EMG relaxation technique;
5. preliminary training in brainwave frequency control such that the subject can reliably produce predominantly alpha or theta wave EEG frequency as determined by certified biofeedback practitioner; and
6. successful training in brainwave inter/intra hemispheric synchrony.

The following is the text of a typical hypnotic induction session that may be used for the training referred to above:

Typical hypnotic trance induction

"As I listen to the voice anchoring me firmly to the ground, I imagine floating in the springtime sky. The warm air carries me aloft like a kite. I can hear the sounds of children playing and feel warm and contented, away from all of life's problems. Floating pleasantly in the air there is nothing to do. It feels so good to be floating, refreshed and relaxed.

"Now I am imagining an old oak staircase in a large old house. The staircase has 20 steps. It is covered with a rich thick carpet. With each step I take, I feel more deeply relaxed. The old oak bannister has been used by many people in the past to be more and more relaxed."

Trance induction

"Counting to twenty, I am going down the staircase, letting the voice anchor me, with each step, becoming more and more deeply relaxed. 1 ... 2 ... 3 ... deeper and deeper relaxed ... 4 ... 5 ... 6 ... deeper and deeper relaxed ... 7 ... 8 ... 9 ... 10 ... halfway to the bottom of the staircase, more and more deeply relaxed. 11 ... 12 ... 13 ... 14 ... 15 ... deeper and deeper relaxed. Any muscle tension, sounds, or other distractions can simply pass through my mind ... 16 ... 17 . .. deeper and deeper relaxed ... 18 ... 19 ... 20 ....

"I am now standing in a beautiful hallway. There is a door way across the hall. I walk across, open the door. I see the room opens onto a meadow. I walk across the room, open the door and go outside. It is a nice spring day. The temperature is perfectly warm. There is an old oak tree in the meadow. I walk over to it and sit down. The old oak tree has been here for thousands of years and is very wise. Its roots go very deeply into the earth. It has seen many people and situations come and go. And as I lean against it, I begin to draw from its strength and wisdom. Sitting here next to the tree feels very good.

"I am getting in touch with the wise part of myself. The old oak tree can help me solve my own problems either now or in the days to come. Even solutions to problems I have been working on for awhile may come to my mind as a result of sitting here next to it. I know that in the future I can return to this old oak tree and use it often for strength and wisdom.

"As I sit here leaning on the old oak tree, gathering its wisdom and security, it seems as if a great deal of time has passed and I feel even more refreshed and secure than before.

"I send out warmth and security to everyone I know, to all mankind."

Hypnotic trance ending

"As I get up to walk back to the house, I notice how good I feel. Now, as I return to the house, I open the door, walk back through the room to the hallway at the bottom of the stairs. As I begin to walk back up the staircase I will be returning to my usual state of awareness yet relaxed and energized. Counting backward from 20, I will begin ascending the staircase ... 20 ... 19 ... 18 ... 17 ... 16 ... 15 ... 14 ... 13 ... 12 ... 11 ... 10 ... halfway to my usual state of awareness 9 ... 8 ... 7 ... 6 ... 5 ... 4 ... when I reach one I will begin opening my eyes and returning to my usual state of awareness yet relaxed and energized ... 3 ... 2 ... 1 .... I can open my eyes now."

It is to be understood that the suggestions set forth in Charts 1 and 2 hereof, and the corresponding text, are exemplary only. Other types and combinations of suggestions and sensory stimuli, and other specific suggestive narratives, may be employed without departing from the principle of the invention.

Many people have no response (i.e., a flat baseline level throughout) to the tape. Hence, the invention may be used as a diagnostic process to ascertain whether or not a person has a response and to characterize the response. However, subjects who initially exhibit no response may be treated to respond through use of the training procedures described above and repeated guided imagery while monitoring blood response to make successive approximations to that person's ideal guided images.

Once stimuli that increase IL-1 for a given subject have been identified by the aforedescribed diagnostic procedure, those stimuli may be employed in a treatment procedure. In accordance with the present invention, the preferred treatment procedure comprises first administering a relaxation technique, then providing stimuli, e.g., by an audio tape message, of the type that have been found to be effective in producing desired changes in the subject, e.g., increasing the effective level of IL-1. The messages that are effective may vary with the subject's history, so it may be desirable to create a new list periodically. The relaxation technique may be any of a variety of well known techniques, including listening to audio relaxation messages such as those described herein, with or without biofeedback. Moreover, biofeedback may be provided while the stimuli are administered in order to ensure that relaxation continues while IL-1 production is being stimulated. This is important because relaxation tends to promote the effectiveness of IL-1 stimulation.

It has been observed that in some subjects, IL-1 response is delayed by 10-30 minutes, and remains elevated beyond the time of the tape being played. This correlation with the behavioral intervention is a positive desired effect. In vitro incubation studies indicate that IL-1 administration to fibroblasts or synoviocytes over the course of several hours leads to a release of the cytokine IL-6. Thence, modulation of IL-1 results in modulation of IL-6 in the time frame of several hours when the overall level of IL-1 is altered for that time period. Also, it is well established that the level of IL-1 modulates IL-2 within the human body; thence, alteration of IL-1 levels by this technique when prolonged over minutes to hours results in alteration of IL-2. While the present invention has been illustrated by specific implementations to stimulate the production of the hormone IL-1, it could similarly be used to stimulate the production of IL-2 and IL-6, and other hormones, as well as IL-1. The same method and apparatus might also be used to reduce the level of a hormone without departing from the principles of the present invention.

The invention comprehends variations in the aforedescribed procedures that may increase their effectiveness. For example, real time analysis of IL-1 levels would permit immediate feedback as to the effectiveness of a particular stimulus, resulting in more rapid treatment. Treatment messages may be integrated with relaxation techniques, as by integrating audio stimuli with prerecorded audio relaxation messages The stimulus need not be audio or video, as a clinician making suggestions for thought or behavior would also be an applicable stimulus. Also, assuming a specific area of the brain is responsible for the IL-1 increase effect, direct control of this area may be achieved utilizing the blood monitoring technique in conjunction with a high resolution brain electrical activity tracking device such as is available via evoked electrical potential mapping, or evoked or endogenus magnetic or electrical potentials mapping.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

I claim:

1. A method for determining the relationship between selected non-invasive sensory stimuli supplied to an animal subject and the level of cytokines in the circulatory system of that subject, comprising:
    (a) periodically taking discrete samples of the blood of the subject at known times;
    (b) while said samples are being taken, supplying to said subject one or more of said selected non-invasive stimuli at known times;
    (c) measuring the amount of said cytokines in said discrete samples; and
    (d) correlating the amount of said cytokines in said discrete samples with the time of occurrence of said selected non-invasive stimuli supplied to said subject so as to identify the relationship therebetween.

2. A method for determining the relationship between selected non-invasive sensory stimuli supplied to an animal subject and the level of a selected hormone in the circulatory system of that subject, comprising:
    (a) periodically taking discrete samples of the blood of the subject at known times;
    (b) while said samples are being taken, supplying to said subject one or more of said selected non-invasive stimuli at known times;
    (c) measuring the amount of said selected hormone in said discrete samples;
    (d) correlating the amount of said selected hormone in said discrete samples with the time of occurrence of said selected non-invasive stimuli supplied to said subject so as to identify the relationship therebetween; and
    (e) measuring the subject's state of relaxation and providing to the subject an indication representative thereof while steps (a) and (b) are being performed.

3. The method of claim 2, wherein said measuring the subject's state of relaxation comprises measuring skin temperature and said providing comprises producing an audio sound representative of said skin temperature.

4. The method of claim 2, wherein said measuring of the subject's state of relaxation comprises measuring the subject's frontalis EMG and said providing comprises producing an audio sound representative of the amplitude of selected components of said frontalis EMG.

5. The method of claim 2, wherein said measuring of the subject's state of relaxation comprises measuring the subject's EEG and said providing comprises producing an audio sound representative of selected EEG evoked potentials.

6. A method for determining the relationship between selected non-invasive sensory stimuli supplied to an animal subject and the level of a selected hormone in the circulatory system of that subject, comprising:
    (a) periodically taking discrete samples of the blood of the subject at known times;
    (b) while said samples are being taken, supplying to said subject one or more of said selected non-invasive stimuli at known times;
    (c) measuring the amount of said selected hormone in said discrete samples;
    (d) correlating the amount of said selected hormone in said discrete samples with the time of occurrence of said selected non-invasive stimuli supplied to said subject so as to identify the relationship therebetween; and
    (e) applying a relaxation procedure to the subject.

7. A method for controlling the level of cytokines in the circulatory system of an animal subject in a predetermined manner, comprising supplying to said subject one or more selected non-invasive sensory stimuli found to have caused a predetermined change in the level of said cytokines in said subject.

8. The method of claim 7, wherein said stimuli are determined in the following manner:
    (a) periodically taking discrete samples of the blood of the subject at known times;
    (b) while said samples are being taken, supplying to said subject one or more of said selected stimuli at known times;
    (c) measuring the amount of said selected hormone in said discrete samples; and
    (d) correlating the amount of said selected hormone in said discrete samples with the time of occurrence of said selected stimuli supplied to said subject so as to identify the relationship therebetween.

9. The method of claim 8, wherein said measuring the amount of said selected hormone in said discrete samples includes using a technique accurate to about 1 to 5 picograms per cc.

10. A method for controlling the level of a selected hormone in the circulatory system of an animal subject in a predetermined manner, comprising supplying to said subject one or more selected non-invasive sensory stimuli found to have caused a predetermined change in the level of said hormone in said subject, said stimuli being determined in the following manner:
  (a) periodically taking discrete samples of the blood of the subject at known times;
  (b) while said samples are being taken, supplying to said subject one or more of said selected non-invasive stimuli at known times;
  (c) measuring the amount of said selected hormone in said discrete samples; and
  (d) correlating the amount of said selected hormone in said discrete samples with the time of occurrence of said selected non-invasive stimuli supplied to said subject so as to identify the relationship therebetween; and
  (e) applying a relaxation procedure to the subject.

11. An apparatus for determining the relationship between selected non-invasive sensory stimuli supplied to an animal subject and the level of a selected hormone in the circulatory system of that subject, comprising:
  (a) sampling means for periodically taking discrete samples of the blood of the subject at known times;
  (b) stimulus means for supplying to said subject one or more of said selected non-invasive stimuli at known times while said samples are being taken;
  (c) analysis means for measuring the amount of said selected hormone in said discrete samples;
  (d) means for recording the amount of said selected hormone in said discrete samples as a function of the time of occurrence of said selected non-invasive stimuli so as to identify the relationship therebetween; and
  (e) biofeedback means for measuring the subject's state of relaxation and providing to the subject an indication representative thereof.

12. The apparatus of claim 11, wherein said biofeedback means comprises means for measuring the skin temperature of the subject and producing an audio sound representative thereof.

13. The apparatus of claim 11, wherein said biofeedback means comprises means for measuring the subject's frontalis EMG and producing an audio sound representative of the amplitude of selected components of said frontalis EMG.

14. The apparatus of claim 11, wherein said biofeedback means comprises means for measuring the subject's EEG and producing an audio sound representative of selected EEG evoked potentials.

15. An apparatus for controlling the level of a selected hormone in the circulatory system of an animal subject in a predetermined manner, comprising:
  (a) sampling means for periodically taking discrete samples of the blood of the subject at known times;
  (b) stimulus means for supplying to said subject one or more of said selected non-invasive stimuli at known times while said samples are being taken;
  (c) analysis means for measuring the amount of said selected hormone in said discrete samples;
  (d) means for recording the amount of said selected hormone in said discrete samples as a function of the time of occurrence of said selected non-invasive stimuli so as to identify a relationship therebetween; and
  (e) means for supplying to the subject those of said selected non-invasive stimuli shown by steps (a) through (d) to cause a desired change in the level of said selected hormone in the circulatory system of the subject.

16. The apparatus of claim 15, further comprising means for applying a relaxation procedure to said subject.

17. The apparatus of claim 15, wherein said selected hormone comprises the immune-regulating cylokine IL-1.

18. The apparatus of claim 15 wherein said stimuli comprise audio signals.

19. A method for determining the relationship between selected non-invasive sensory stimuli supplied to an animal subject and the level of the immune-regulating cytokine IL-1 in the circulatory system of that subject, comprising:
  (a) periodically taking discrete samples of the blood of the subject at known times;
  (b) while said samples are being taken, supplying to said subject one or more of said selected non-invasive stimuli at known times;
  (c) measuring the amount of IL-1 in said discrete samples; and
  (d) correlating the amount of IL-1 in said discrete samples with the time of occurrence of said selected non-invasive stimuli supplied to said subject so as to identify the relationship therebetween.

20. A method for determining the relationship between selected audio sound sensory stimuli supplied to an animal subject and the level of a selected hormone in the circulatory system of that subject, comprising:
  (a) periodically taking discrete samples of the blood of the subject at known times;
  (b) while said samples are being taken, supplying to said subject one or more selected audio sounds at known times;
  (c) measuring the amount of said selected hormone in said discrete samples; and
  (d) correlating the amount of said selected hormone in said discrete samples with the time of occurrence of said selected audio sounds supplied to said subject so as to identify the relationship therebetween.

21. A method for controlling the level of the immune-regulating cytokine IL-1 in the circulatory system of an animal subject in a predetermined manner, comprising supplying to said subject one or more selected non-invasive sensory stimuli found to have caused a predetermined change in the level of IL-1 in said subject.

22. A method for controlling the level of a selected hormone in the circulatory system of an animal subject in a predetermined manner, comprising supplying to said subject one or more selected audio sound sensory stimuli found to have caused a predetermined change in the level of said hormone in said subject.

23. An apparatus for determining the relationship between selected non-invasive sensory stimuli supplied to an animal subject and the level of the immune-regulating cytokines IL-1 in the circulatory system of that subject, comprising:
  (a) sampling means for periodically taking discrete samples of the blood of the subject at known times;
  (b) stimulus means for supplying to said subject one or more of said selected non-invasive stimuli at known times whole said samples are being taken;

(c) analysis means for measuring the amount of IL-1 in said discrete samples; and (d) means for recording the amount of IL-1 in said discrete samples as a function of the time of occurrence of said selected non-invasive stimuli so as to identify the relationship therebetween.

24. An apparatus for determining the relationship between selected audio signal stimuli supplied to an animal subject and that level of a selected hormone in the circulatory system of that subject, comprising:

(a) sampling means for periodically taking discrete samples of the blood of the subject at known times;

(b) stimulus means for supplying to said subject one or more of said selected audio signal stimuli at known times whole said samples are being taken;

(c) analysis means for measuring the amount of said selected hormone in said discrete samples; and (d) means for recording the amount of said selected hormone in said discrete samples as a function of the time of occurrence of said selected audio signal stimuli so as to identify the relationship therebetween.

25. A method for controlling the level of a selected hormone in the circulatory system of an animal subject in a predetermined manner, comprising:

(a) supplying to said subject one or more selected non-invasive stimuli at known times;

(b) while said selected non-invasive stimuli are being supplied, taking discrete samples of the blood of the subject at known times;

(c) measuring the amount of said selected hormone in said discrete samples;

(d) determining whether there is a relationship between the application of said selected non-invasive stimuli and the level of said selected hormones in the circulatory system of the subject; and (e) supplying to the subject those of said selected non-invasive stimuli shown by steps (a) through (d) to cause a desired change in the level of said selected hormone in the circulatory system of the subject.

* * * * *